United States Patent
Straetmans et al.

(10) Patent No.: US 7,416,722 B2
(45) Date of Patent: Aug. 26, 2008

(54) CONCENTRATED, AQUEOUS SOLUTIONS OF P-METHOXYBENZOIC ACID FOR USE IN COSMETIC AND DERMATOLOGIC FORMULATIONS

(75) Inventors: Udo Straetmans, Hamburg (DE); Jan Jänichen, Hamburg (DE); Wilfried Petersen, Hamburg (DE); Michael Kinder, Hamburg (DE); Christopher H. Johnson, Hazlet, NJ (US); Garrett S. Reynolds, Hazlet, NJ (US)

(73) Assignee: Dr. Straetmans GmbH, Hamburg (DE)

( * ) Notice: Subject to any disclaimer, the term of this patent is extended or adjusted under 35 U.S.C. 154(b) by 214 days.

(21) Appl. No.: 11/396,856

(22) Filed: Apr. 3, 2006

(65) Prior Publication Data

US 2006/0229291 A1    Oct. 12, 2006

(30) Foreign Application Priority Data

Apr. 8, 2005    (EP) .................... 05007721

(51) Int. Cl.
| | | |
|---|---|---|
| *A61L 9/01* | (2006.01) | |
| *A61L 9/04* | (2006.01) | |
| *A61L 9/012* | (2006.01) | |
| *A61L 9/013* | (2006.01) | |
| *A61L 9/014* | (2006.01) | |
| *A61L 9/05* | (2006.01) | |

(52) U.S. Cl. .................................... 424/76.4
(58) Field of Classification Search ................. 424/76.4
See application file for complete search history.

(56) References Cited

U.S. PATENT DOCUMENTS

| 6,245,843 | B1 * | 6/2001 | Kobayashi et al. .......... 524/109 |
| 2004/0167195 | A1 | 8/2004 | Muller ....................... 514/400 |
| 2005/0245608 | A1 * | 11/2005 | Baranger et al. ............ 514/546 |

FOREIGN PATENT DOCUMENTS

| FR | 2834459 | 7/2003 |
| WO | WO 8706827 | 11/1987 |

OTHER PUBLICATIONS

Gulyaeva, Nellie; Alexander Zaslavsky, Arnon Chait, and Boris Zaslavsky. "Measurement of the Relative Hydrophobicity of Organic Compounds Without Organic Solvent. Effects of Salt Composition and pH on Organic Acids and Nonionic Compounds." Journal of Pharmaceutical Sciences, vol. 90, No. 9, Sep. 2001, pp. 1366-1374.

* cited by examiner

*Primary Examiner*—Johann Richter
*Assistant Examiner*—Courtney Brown
(74) *Attorney, Agent, or Firm*—Roberts & Roberts, LLP

(57) ABSTRACT

The present invention is related to concentrated aqueous solutions of p-methoxybenzoic acid and their production.

20 Claims, No Drawings

CONCENTRATED, AQUEOUS SOLUTIONS OF P-METHOXYBENZOIC ACID FOR USE IN COSMETIC AND DERMATOLOGIC FORMULATIONS

BACKGROUND OF THE INVENTION

1. Field of the Invention

The invention is related to concentrated aqueous solutions of p-methoxybenzoic acid and their production.

2. Description of the Related Art

Optimizing production processes to save time, space, or resources like energy or manpower define the area of technical controlling and are part of the most effective possibilities to improve the manufacturing industry's cost situation.

Under the pressure to reduce the costs per unit, it is being continuously attempted to construct work processes more efficiently on all levels. Apart from improving internal processes, external partners like suppliers of raw materials are more and more included in optimizing production processes. Thus e.g., on-time supply of raw materials in product-compatible trading units may shift stock capacities to the road, may improve the workflow considerably, and add to a significant reduction in costs per unit.

An important aspect, which can play a major role especially in larger production units, is a raw material's state of aggregation. While fluid or gaseous materials can be fed into the production process easily and in adjustable doses using pumps, adding solid raw materials is usually related to a weighing process and open product handling. The last point mentioned is also related to safety aspects, as the personnel working in the manufacturing process is exposed to the open product.

Solid and heavily soluble raw materials, which have to be solubilized before being processed, need additional requirements for the production processes, as these solubilizing processes often demand additional energy, need a lot of time and in many cases additional vessels to mix the substances. That is why a lot of heavily soluble raw-materials are liked to be used in the laboratory or in development, but fail in production processes due to their difficult handling.

Against this background, fluid and concentrated formulations of heavily soluble raw materials if they don't contradict the quality requirements of the final product, are obviously advantageous, both technically as well as economically, and therefore the target of the invention.

DESCRIPTION OF THE INVENTION p-Methoxybenzoic acid has become increasingly significant as multi-functional raw material in the cosmetic as well as the food industry in recent years. Thus, for example, aqueous compositions and their use in cosmetics are known, which contain 1-30% p-methoxybenzoic acid and up to 50% of one or more polyols, like glycerol, (see FR 2834459, claims 1-24). One base, like sodium hydroxide, and citric acid is also contained herein. The compositions have a pH of 5.2.

Apart from its main function as masking agent and aroma component, this raw material's interesting qualities of biologically stabilizing cosmetic and dermatologic formulations as well as being an active ingredient against specific germs in skin- and hair-care products have attracted a lot of attention. The solubility of p-methoxybenzoic acid in aqueous systems is very low and the solubilizing-process itself is extraordinarily slow. This complicates the use of p-methoxybenzoic acid in cosmetic formulas.

To go around this difficulty it usually pays off to use the form of more soluble salts. The potassium and sodium salts of p-methoxybenzoic acid are easily dissolved initially in an aqueous phase and can be worked into the formulation. The salts, when acidified afterwards, can be transformed back into the active p-methoxybenzoic acid. Nevertheless, there seem to exist forms of crystals of these salts, which have a lower solubility, which crystallize irreversibly after some time, especially in high concentrations and in the cold.

The manufacturing and storage of higher concentrated, aqueous solutions have therefore not been possible up to now, but this would mean a considerable, technical development. Surprisingly, it has now been found, that the disadvantages of the technical state-of-the-art can be abolished by providing a liquid, approximately neutralized combination according to the invention.

In these solutions crystals may form at low temperatures, but in contrast to simple aqueous systems, will reversibly form a clear and homogeneous solution when warmed up to room temperature.

Glycerol or glycols, like e.g. propylene glycol, butylene glycol, dipropylene glycol, or 2-methylpropanediol belong to the group of polyols, which can lead to stabilization according to the present invention. Esters of polyglycerol, like e.g. polyglyceryl-10 laurate, or esters of sorbitan, like e.g. sorbitan laurate, are useful, as well. Glycerol is especially suitable here. Salts of adequate organic acids, which are suitable for a stabilization according to the present invention, are the sodium and potassium salts of levulinic acid, of lactic acid, or of citric acid as well as the ammonium salts of the general type $HNR_3^+$, where R=H, alkyl, hydroxyalkyl. The potassium and sodium salts of levulinic acid are preferred especially.

p-Methoxybenzoic acid can be obtained under the trade name of DERMOSOFT® 688 from Dr. Straetmans GmbH in a cosmetical grade. The solubility of p-methoxybenzoic acid in water is approximately 05 g/l. For use in a cosmetic formulation the product is usually brought into solution with sodium hydroxide or potassium hydroxide in a small amount of water at warm temperatures and worked into an aqueous phase. To evolve the spectrum of effects of p-methoxybenzoic acid completely, afterwards the formula should be re-acidified to a pH-value of 5.5. The literature describes the salts of p-methoxybenzoic acid to be easily soluble in water, but practice shows, that an inclusion of higher concentrated solutions of sodium and potassium salts for a longer period of time and/or at lower temperatures can lead to a crystallization of the salts. Surprisingly, when afterwards warmed up to room temperature, these salts do not go back into solution again. This may show, that the initial homogenous solutions are merely meta-stable systems.

According to the present state-of-the-art, the solubility of the salts can be improved by adding foreign ionic salts. Following the theory, adding such salts improves the chemical activity and thus the solubilizing capacity of the solvent system. According to the theory, adding common ionic salts on the contrary, as well as the addition of solvents, which are not at all or only slightly able to solvate ions, should reduce the solubility of the salts, which have to be dissolved.

Surprisingly, and not to be expected according to the theory, it was found out that the solubility of the sodium and potassium salts of p-methoxybenzoic acid in the presence of organic solvents of the class of polyols can be improved. Glycerol has proven to be especially suitable, but also glycols, like propylene glycol, butylene glycol, dipropylene glycol, or 2-methylpropanediol were able to improve the solubility. Solubilizers of the class of esters of polyglycerol, like e.g. polyglyceryl-10 laurate, or of the class of esters of sorbitan, like e.g. sorbitan laurate are suitable, as well.

Thus, the following formulas for example proved to be thermodynamically stable:

Formula 1

| | |
|---|---|
| 5 g | p-methoxybenzoic acid |
| 30 g | glycerol |
| 15.0 g | 10% sodium hydroxide in water |
| add 100 g | water | pH = 10-12

Formula 2

| | |
|---|---|
| 5 g | p-methoxybenzoic acid |
| 31.5 g | polyglyceryl-10 laurate |
| 14.0 g | 10% sodium hydroxide in water |
| add 100 g | water | pH = 7.5

The presence of salts of organic acids improves the solubility of the mentioned salts of the p-methoxybenzoic acid also. Here especially sodium levulinate and potassium levulinate as well as ammonium salts of levulinic acid of the general type $HNR_3^+$, where R=H, alkyl, hydroxyalkyl, have proven to be suitable, but the relevant lactate and citrate have proven to be useful, as well. The solubility of the salts of p-methoxybenzoic acid is improved most effectively, thus finding a remedy for the present technical state, by combining polyols and the mentioned salts of the levulinic acid.

The following formulas are mentioned here exemplary:

Formula 3

| | |
|---|---|
| 5 g | p-methoxybenzoic acid |
| 21 g | levulinic acid |
| ~19 g | 45% aqueous sodium hydroxide |
| 50 g | glycerol |
| add 100 g | water | pH = 7.5

Formula 4

| | |
|---|---|
| 7.5 g | p-methoxybenzoic acid |
| 22.5 g | levulinic acid |
| ~21.5 g | 45% aqueous sodium hydroxide |
| 25 g | glycerol |
| add 100 g | water | pH = 7.5

The mixtures mentioned as per the invention are stable to be stored over a long period of time and show no tendency whatsoever to crystallize irreversibly. Furthermore, these mixtures show advantageous characteristics for equally well-balanced stabilizations of cosmetic formulations against the growths of bacteria, yeasts, and fungi.

The mixtures can be manufactured advantageously by first dispersing the p-methoxybenzoic acid in the polyol and afterwards by adding an amount of an aqueous solution of the base, which is stochiometric to the total amount of acids. In mixtures, which contain further organic acids, these acids are used to adjust the pH-value of the mixture to a value between 7.0 and 8.0. The subject of the present invention is therefore aqueous solutions of the sodium and/or potassium salts of p-methoxybenzoic acid and/or ammonium salts of the general type $HNR_3^+$, where R=H, alkyl, hydroxyalkyl of the same, which have been stabilized by the addition of polyols and/or sodium or potassium salts, or ammonium salts of the general type $HNR_3^+$, where R=H, alkyl, hydroxyalkyl of levulinic acid, lactic acid, or citric acid, as well as their manufacturing and their usage as a perfume or masking agent, aromatizing, and biologically stabilizing cosmetic and dermatologic formulations to treat, groom, or clean the skin and/or hair as well as in products of decorative cosmetics.

What is claimed is:

1. A liquid, composition comprising:
   a) 5-15 weight % p-methoxybenzoic acid, or salt thereof:
   b) 5-60 weight % of water; and
   at least one of c) and/or d):
   c) 20-55 weight % one or more of an organic acid and/or their salts;
   d) 20-60 weight % one or more of a polyol, an ester of polyglycerol and an ester of sorbitan; said composition having a pH of 7.0-8.0.

2. The composition of claim 1 comprising:
   a) 5 weight % to 10 weight % sodium salts of p-methoxybenzoic acid;
   b) 5 weight % to 55 weight % water;
   c) 20 weight % to 30 weight % sodium levulinate
   d) 20 weight % to 55 weight % glycerol.

3. A method of producing a composition comprising
   a) 5 weight % to 10 weight % sodium salts of p-methoxybenzoic acid;
   b) 5 weight % to 55 weight % water;
   c) 20 weight % to 30 weight % sodium levulinate
   d) 20 weight % to 55 weight % glycerol; the method comprising dispersing p-methoxybenzoic acid in glycerol, subsequently adding an amount of aqueous sodium hydroxide which is equimolar to the calculated total amount of acids, adjusting the pH-value to 7.0-8.0 with levulinic acid and adding the remaining water.

4. The composition of claim 1 wherein component c) comprises a sodium salt of levulinic acid, a potassium salt of levulinic acid, a sodium salt of lactic acid, a potassium salt of lactic acid, a sodium salt of citric acid, a potassium salt of citric acid, or an ammonium salts of the formula $HNR_3^+$, wherein R=H, alkyl, hydroxyalkyl.

5. The composition of claim 1 wherein component d) comprises a glycol, a glycerol, or an ester of sorbitan.

6. The composition of claim 1 wherein component d) comprises propylene glycol, butylene glycol, dipropylene glycol, 2-methylpropanediol, polyglyceryl-10 laurate, or sorbitan laurate.

7. The composition of claim 1 wherein component c) comprises a sodium salt of levulinic acid, a potassium salt of levulinic acid, a sodium salt of lactic acid, a potassium salt of lactic acid, a sodium salt of citric acid, a potassium salt of citric acid, or an ammonium salts of the formula $HNR_3^+$, wherein R=H, alkyl, hydroxyalkyl; and wherein component d) comprises propylene glycol, butylene glycol, dipropylene glycol, 2-methylpropanediol, polyglyceryl-10 laurate, or sorbitan laurate.

8. The composition of claim 1 comprising:

| | |
|---|---|
| 5 g | p-methoxybenzoic acid |
| 30 g | glycerol |
| 15.0 g | 10% sodium hydroxide in water |
| 100 g | water. |

9. The composition of claim 1 comprising:

| | |
|---|---|
| 5 g | p-methoxybenzoic acid |
| 31.5 g | polyglyceryl-10 laurate |
| 14.0 g | 10% sodium hydroxide in water |
| 100 g | water | said composition having a pH = 7.5.

10. The composition of claim 1 comprising:

| | |
|---|---|
| 5 g | p-methoxybenzoic acid |
| 21 g | levulinic acid |
| 19 g | 45% aqueous sodium hydroxide |
| 50 g | glycerol |
| 100 g | water | said composition having a pH = 7.5.

11. The composition of claim 1 comprising:

| | |
|---|---|
| 7.5 g | p-methoxybenzoic acid |
| 22.5 g | levulinic acid |
| 21.5 g | 45% aqueous sodium hydroxide |
| 25 g | glycerol |
| 100 g | water | said composition having a pH = 7.5.

12. A perfume, masking agent, aromatizing, cosmetic or dermatologic formulation which comprises a liquid, composition comprising:
 a 5-15 weight % p-methoxybenzoic acid, or salt thereof;
 b) 5-60 weight % of water; and at least one of c) and/or d):
 c) 20-55 weight % one or more of an organic acid and/or their salts;
 d) 20-60 weight % one or more of a polyol, an ester of polyglycerol and an ester of sorbitan; said composition having a pH of 7.0-8.0.

13. The formulation of claim 12 wherein the liquid, composition comprises:
 a) 5 weight % to 10 weight % sodium salts of p-methoxybenzoic acid;
 b) 5 weight % to 55 weight % water;
 c) 20 weight % to 30 weight % sodium levulinate
 d) 20 weight % to 55 weight % glycerol.

14. The formulation of claim 12 wherein component c) comprises a sodium salt of levulinic acid, a potassium salt of levulinic acid, a sodium salt of lactic acid, a potassium salt of lactic acid, a sodium salt of citric acid, a potassium salt of citric acid, or an ammonium salts of the formula $HNR_3^{30}$, wherein R=H, alkyl, hydroxyalkyl.

15. The formulation of claim 12 wherein component d) comprises a glycol, a glycerol, or an ester of sorbitan.

16. The formulation of claim 12 wherein component d) comprises propylene glycol, butylene glycol, dipropylene glycol, 2-methylpropanediol, polyglyceryl-10 laurate, or sorbitan laurate.

17. The formulation of claim 12 wherein the liquid, composition comprises:

| | |
|---|---|
| 5 g | p-methoxybenzoic acid |
| 30 g | glycerol |
| 15.0 g | 10% sodium hydroxide in water |
| 100 g | water. |

18. The formulation of claim 12 wherein the liquid, composition comprises:

| | |
|---|---|
| 5 g | p-methoxybenzoic acid |
| 31.5 g | polyglyceryl-10 laurate |
| 14.0 g | 10% sodium hydroxide in water |
| 100 g | water | said composition having a pH = 7.5.

19. The formulation of claim 12 wherein the liquid, composition comprises:

| | |
|---|---|
| 5 g | p-methoxybenzoic acid |
| 21 g | levulinic acid |
| 19 g | 45% aqueous sodium hydroxide |
| 50 g | glycerol |
| 100 g | water | said composition having a pH = 7.5.

20. The formulation of claim 12 wherein the liquid, composition comprises:

| | |
|---|---|
| 7.5 g | p-methoxybenzoic acid |
| 22.5 g | levulinic acid |
| 21.5 g | 45% aqueous sodium hydroxide |
| 25 g | glycerol |
| 100 g | water | said composition having a pH = 7.5.

* * * * *